United States Patent [19]

Colignon et al.

[11] Patent Number: 5,391,783
[45] Date of Patent: Feb. 21, 1995

[54] PROCESS FOR THE PRODUCTION OF LIGHT-COLORED PASTES OF α-SULFOFATTY ACID ALKYL ESTER ALKALI METAL SALTS

[75] Inventors: Dietmar Colignon, Erkrath; Erich Dorra, Duesseldorf; Herbert Lepper, Hilden; Guenter Panthel, Haan; Francois Pierron, Annecy; Wolfgang Schmidt, Monheim; Norbert Wrede, Dusseldorf, all of Germany

[73] Assignee: Henkel Kommanditgesellschaft auf Aktien, Duesseldorf, Germany

[21] Appl. No.: 965,387

[22] PCT Filed: May 21, 1991

[86] PCT No.: PCT/EP91/00941

§ 371 Date: Dec. 14, 1992

§ 102(e) Date: Dec. 14, 1992

[87] PCT Pub. No.: WO91/18872

PCT Pub. Date: Dec. 12, 1991

[30] Foreign Application Priority Data

May 30, 1990 [DE] Germany ............... 4017466

[51] Int. Cl.⁶ ............... C07C 303/32
[52] U.S. Cl. ............... 554/98; 554/85; 554/96; 554/97
[58] Field of Search ............... 554/97, 98, 85, 96

[56] References Cited

U.S. PATENT DOCUMENTS

| | | | |
|---|---|---|---|
| 3,251,868 | 5/1966 | Stein et al. | 260/400 |
| 4,102,911 | 7/1978 | Majima et al. | 554/98 |
| 4,404,143 | 9/1983 | Sekiguchi et al. | 260/400 |
| 4,495,092 | 1/1985 | Schmid et al. | 252/589 |
| 4,547,318 | 10/1985 | Kloetzer et al. | 260/400 |
| 4,668,438 | 5/1987 | Pierr et al. | 260/400 |
| 4,695,409 | 9/1987 | Piorr et al. | 260/400 |

FOREIGN PATENT DOCUMENTS

| | | |
|---|---|---|
| 401925 | 5/1970 | Australia ............... 554/97 |
| 2400538 | 7/1974 | Germany . |
| 3123681 | 3/1982 | Germany . |
| 3334517 | 4/1984 | Germany . |
| 3305430 | 8/1984 | Germany . |
| 3319591 | 12/1984 | Germany . |
| 3432324 | 3/1986 | Germany . |
| 3538910 | 5/1987 | Germany . |

*Primary Examiner*—José G. Dees
*Assistant Examiner*—Deborah D. Carr
*Attorney, Agent, or Firm*—Wayne C. Jaeschke; John E. Drach; Henry E. Millson, Jr.

[57] ABSTRACT

In the production of light-colored pastes of α-sulfofatty acid alkyl ester alkali metal salts by reaction of fatty acid alkyl esters with gaseous SO₃, subsequent after-reaction in liquid phase, neutralization with aqueous alkali metal hydroxide solutions and bleaching, effective bleaching can be obtained without any reduction in the washing-active substance content by addition of the hydrogen peroxide during neutralization of the α-sulfofatty acid alkyl ester and subjecting the neutralization product obtained to a temperature-controlled after-reaction.

20 Claims, 1 Drawing Sheet

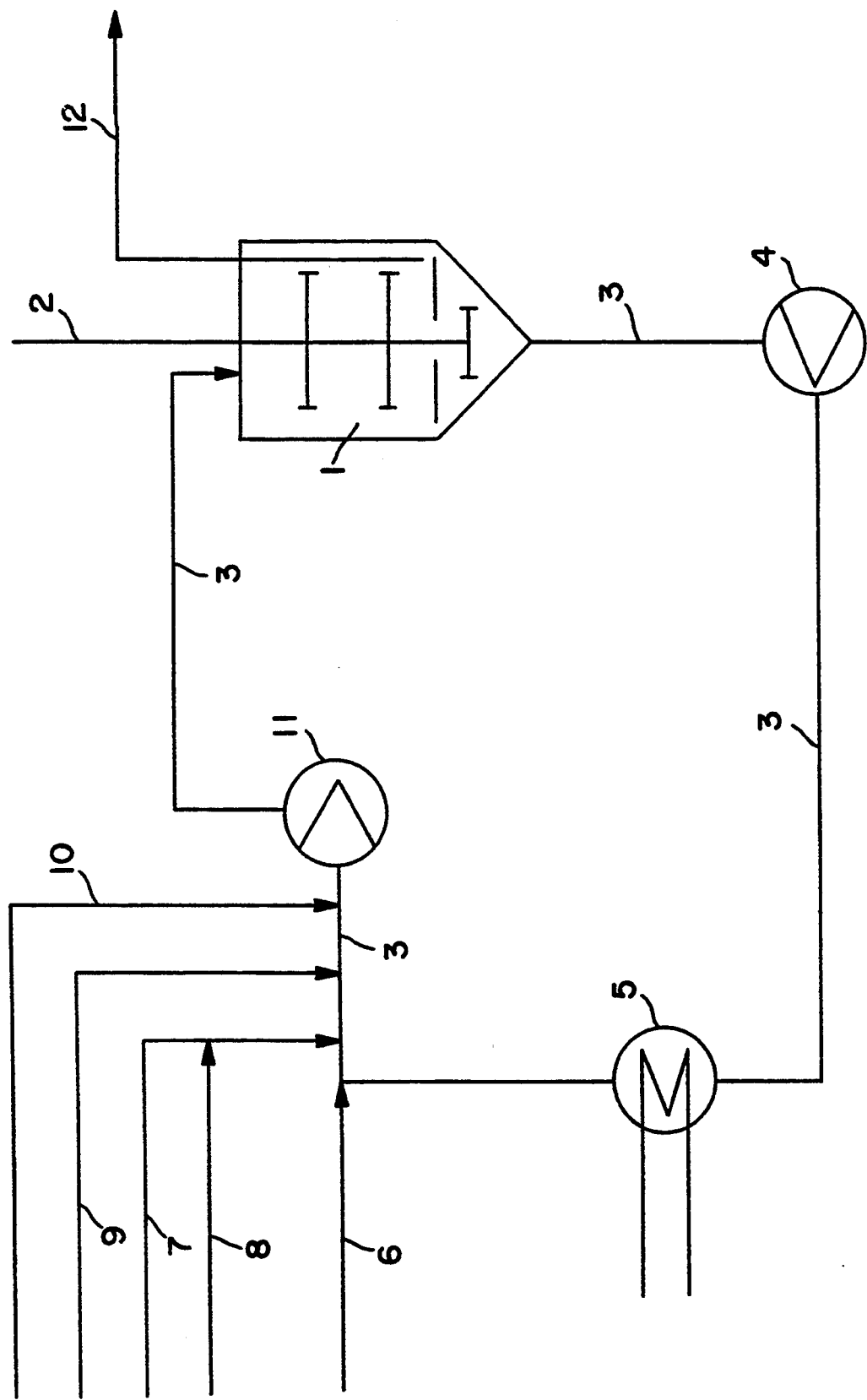

PROCESS FOR THE PRODUCTION OF LIGHT-COLORED PASTES OF α-SULFOFATTY ACID ALKYL ESTER ALKALI METAL SALTS

BACKGROUND OF THE INVENTION

This invention relates to a process for the production of light-colored pastes of α-sulfofatty acid alkyl ester alkali metal salts, in which hydrogen peroxide is used as sole bleaching agent to bleach the sulfonation product during neutralization of the α-sulfofatty acid alkyl ester.

STATEMENT OF RELATED ART

α-Sulfofatty acid alkyl ester alkali metal salts are acquiring increasing significance as surfactants for detergents and cleaning preparations based on renewable natural raw materials. In known processes, the α-sulfofatty acid alkyl ester alkali metal salts are obtained in the form of aqueous solutions or pastes by neutralization of α-sulfofatty acid alkyl esters which may be synthesized by reaction of lower fatty acid alkyl esters with gaseous $SO_3$. In the final analysis, the basis for the production of the α-sulfofatty acid alkyl ester alkali metal salts are fats and oils of natural origin from which the lower fatty acid alkyl esters are obtained by lipolysis and subsequent esterification of the free fatty acids with lower alkanols or by transesterification of the natural triglycerides with lower alkanols. In both reactions, methanol is preferably used as the lower alkanol. The lower fatty acid alkyl esters are mixtures in which $C_{6-22}$ fatty acid residues occur, the chain length distribution being dependent on the origin of the natural fats or oils. In many cases, these fatty acid mixtures are not used for the synthesis as such, but rather in the form of certain fractions. Sulfonation of the fatty acid ester mixtures with gaseous $SO_3$ gives acidic α-sulfofatty acid alkyl esters which are converted into aqueous pastes of α-sulfofatty acid alkyl ester alkali metal salts by neutralization to a pH value of 6 to 8.

The crude α-sulfofatty acid alkyl esters and their alkali metal salts are more or less colored products which generally have to be treated with typical bleaches before and/or after neutralization. Various bleaching processes have become known in connection with the production of light-colored α-sulfofatty acid alkyl ester alkali metal salt solutions and pastes. Combined bleaching processes have been developed for effective product lightening. According to DE-AS 12 34 709, the acidic α-sulfofatty acid alkyl ester is initially treated with aqueous hydrogen peroxide solution in a first bleaching step. The partly bleached sulfonation product is then neutralized before it is exposed to the effect of more hydrogen peroxide solution or aqueous hypochlorite solution in a second bleaching step. According to DE-OS 33 19 591, the neutralized sulfonation product is first bleached with aqueous hypochlorite solution at pH values of 7 to 10. Hydrogen peroxide solution is then added at pH values of $\leq 7$ to stabilize the color values reached. These processes are attended by the disadvantage that the desired high washing active substance contents of the α-sulfofatty acid alkyl ester alkali metal salt pastes, which are reached during neutralization, are reduced again by introduction of the aqueous bleach solutions. In the context of the present invention, washing-active substance (WAS) is understood to be the sum of α-sulfofatty acid alkyl ester alkali metal salt and the α-sulfofatty acid ester always present as secondary product.

One particular difficulty involved in the production and handling of aqueous α-sulfofatty acid alkyl ester alkali metal salt pastes arises out of their viscosity behavior in dependence upon the concentration of washing-active substance. In aqueous compositions, the α-sulfofatty acid alkyl ester alkali metal salts produced by conventional industrial processes (hereinafter also referred to in short as ester sulfonates) only form solutions or suspensions of such low viscosity that they flow sufficiently freely to guarantee uninterrupted completion of industrial processes at WAS contents of up to about 40% by weight and then again beyond solids contents of around 55% by weight. In the intermediate concentration range, i.e. at WAS contents of around 40 to 55% by weight, the aqueous ester sulfonate compositions show extremely high viscosity values, assuming the form of more or less solid gels which can neither be stirred nor pumped. In addition, the lower and upper limits of the individual viscosity maxima can vary by ±5% by weight WAS content. As a result of this particular concentration/viscosity behavior, ester sulfonate pastes having WAS contents above 35 to 40% by weight cannot be obtained simply by neutralization of the acidic α-sulfofatty acid alkyl esters with the calculated quantity of aqueous alkali metal hydroxide solutions using known methods. After the lower limit to the viscosity maximum has been exceeded, the reacting mixture loses its stirrability and miscibility. The lack of stirrability and miscibility prevents adequate and rapid dissipation of the heat of neutralization. Local concentration and temperature peaks initiate unwanted secondary reactions, more particularly cleavage of the ester bonds present in the ester sulfonates, so that undesirably high concentrations of alkali metal disalts of the free α-sulfofatty acids are established in the end product. The subsequent processing of ester sulfonate pastes immobilized by the high increase in viscosity is of course also impaired to the point where it is no longer possible solely as a result of the fact that the aqueous compositions in question can no longer be poured or pumped.

The formation of disalts of the free α-sulfofatty acid alkyl esters is undesirable for several reasons. The disalts show only limited solubility in water and, in addition, have inadequate surface-active properties. Above all, however, disalts as secondary products in ester sulfonate pastes have a considerable viscosity-increasing effect.

There has been no shortage of attempts in the past to eliminate at least most of the unfavorable effects caused by the particular concentration/viscosity behavior of the ester sulfonates and the unwanted formation of α-sulfofatty acid disalts. Thus, it has been proposed to improve the flow behavior of aqueous ester sulfonate compositions by the addition of flow aids. According to DE-OS 33 05 430, aliphatic alcohols containing 8 to 40 carbon atoms and 1 to 6 hydroxyl groups, alkylphenols and adducts of up to 20 mol ethylene oxide and/or propylene oxide with the alcohols and alkylphenols mentioned are used as viscosity regulators.

In connection with the unwanted formation of disalts during working up of the acidic α-sulfofatty acid alkyl esters, DE-OS 31 23 681 describes a process in which the neutralizing treatment is carried out in two steps. In the first step, neutralization is carried out to a pH value of 2.5 to 4 with a 15 to 50% by weight alkali metal hydroxide solution in the presence of a $C_{1-4}$ alcohol, preferably methanol, in a quantity of 5 to 20% by weight, based on the weight of the sulfonated product, before a final pH value of 6 to 7 is adjusted in the second neutralization step using a more heavily diluted alkali metal hydroxide solution. It is said to be possible by this process to reduce the disalt content of the ester sulfonate compositions to 5% by weight, based on washing-active substance, or less. A serious disadvantage of this process is obvious: the ester sulfonate pastes produced in this way contain considerable quantities of alcohol which are troublesome in the production of detergent mixtures by spray drying insofar as they can cause unwanted pluming. To limit the alcohol content of the end products, DE-OS 33 34 517 suggests carrying out the optional bleaching step and neutralization of the crude $\alpha$-sulfofatty acid alkyl esters in the presence of such a quantity of a lower alcohol that an aqueous slurry containing 30 to 40% by weight and, based on the weight of the $\alpha$-sulfofatty acid ester salt, 5 to 15% by weight of a lower alcohol sulfate and 8 to 40% by weight of the lower alcohol is obtained. Finally, the aqueous slurry is said to be concentrated to such an extent that it contains 40 to 65% by weight $\alpha$-sulfofatty acid ester salt, 2 to 10% by weight lower alcohol sulfate and at most 2% by weight lower alcohol.

According to DE-OS 34 32 324, the disalt content of $\alpha$-sulfofatty acid alkyl ester alkali metal salt pastes can be controlled and reduced by subjecting the crude sulfonation product before treatment with an aqueous medium to a transesterification reaction in which at least 0.5 mol-equivalent alcohol, based on the $SO_3$ which is not used for the $\alpha$-sulfonation, is used. According to DE-OS 35 38 910, $\alpha$-sulfofatty acid alkyl ester salt pastes having solids contents above 35% by weight can be produced by subjecting the crude ester sulfonates to transesterification in accordance with DE-OS 34 32 324 and then establishing solids contents of more than 35% by weight in the aqueous pastes during subsequent working up by neutralization with or without preliminary or subsequent bleaching.

The problem addressed by the present invention was to find a process which would enable the necessary bleaching of the sulfonation products with aqueous bleaching solutions in the production of $\alpha$-sulfofatty acid alkyl ester alkali metal salt pastes to be carried out in such a way that the solids content of the pastes would not be reduced by the bleaching. More particularly, the invention set out to provide a process in which free-flowing and pumpable ester sulfonate pastes having WAS contents of 60% to 70% by weight would be obtained by direct neutralization of the acidic $\alpha$-sulfofatty acid alkyl esters with aqueous alkali metal hydroxide solutions and correspondingly adapted bleaching without any need for the addition of "foreign" substances, such as relatively long chain aliphatic mono- and polyalcohols and alkylene oxide adducts thereof or short-chain alcohols.

BRIEF DESCRIPTION OF THE DRAWING

FIG. 1 is a schematic representation of the neutralization-bleaching process.

DESCRIPTION OF THE INVENTION

The teaching according to the invention is based on the surprising observation that light-colored pastes of $\alpha$-sulfofatty acid alkyl ester alkali metal salts can be obtained without any reduction in the WAS content of the end product providing hydrogen peroxide is added as sole bleaching agent during neutralization of the acidic sulfonation product and the neutralization product is allowed to after-react at elevated temperature. It has also been found that light-colored $\alpha$-sulfofatty acid alkyl ester alkali metal salt pastes having WAS contents of 60 to 70% by weight can be obtained in the absence of viscosity-regulating additives by introducing the acidic sulfonation product together with aqueous alkali metal hydroxide solution and aqueous hydrogen peroxide solution into an already present aqueous phase during neutralization and ensuring that the pH value of the aqueous phase remains within a certain range.

The present invention relates to a process for the production of light-colored pastes of $\alpha$-sulfofatty acid alkyl ester alkali metal salts by reaction of fatty acid alkyl esters with gaseous $SO_3$, subsequent after-reaction in liquid phase, neutralization with aqueous alkali metal hydroxide solutions and treatment with hydrogen peroxide, in which the hydrogen peroxide is added to the $\alpha$-sulfofatty acid alkyl ester during neutralization and the neutralization product obtained is subjected to a temperature-controlled after-reaction.

According to the invention, 0.5 to 3% by weight and preferably 1.5 to 2.5% by weight hydrogen peroxide, based on washing-active substance in the neutralization product, is added during neutralization. The hydrogen peroxide is counted as 100% by weight substance. The hydrogen peroxide is added in the form of 5 to 35% by weight and preferably 10 to 20% by weight aqueous solutions. The temperature-controlled after-reaction of the neutralization product is preferably carried out at 60° to 90° C.

In one particular embodiment of the invention, at least one typical bleach activator is added during or after neutralization, but before the temperature-controlled after-reaction. Suitable bleach activators are, in particular, organic compounds which are capable of forming percarboxylic acids or percarboxylic acid anions with hydrogen peroxide under the conditions of the neutralization step and the temperature-controlled after-reaction. Among these compounds, those which contain N-acyl groups, preferably N-acetyl groups, are particularly suitable. Special examples of preferred bleach activators are tetraacetyl ethylenediamine and tetraacetyl glycoluril. The bleach activators are added to the reaction mixture in quantities of 0.1 to 5% by weight, based on the washing-active substance expected in the neutralization product.

During the temperature-controlled after-reaction, the neutralization product containing hydrogen peroxide and optionally bleach activator is preferably kept at the intended temperature of 60° to 90° C. until it has a Klett color value of $\leq 200$ and preferably $\leq 100$ (as measured on an aqueous solution containing 5% by weight washing-active substance in a 4 cm cuvette with a blue filter at 420 nm).

In certain cases, particularly when fairly strongly colored sulfonation products are to be processed, it may be advisable to add hydrogen peroxide once more to the neutralization product before the beginning of the after-reaction. In that case, generally another 0.1 to 2% by weight and preferably another 0.1 to 0.5% by weight, based on the washing-active substance present, is added.

In another preferred embodiment of the process according to the invention relating to the production of highly concentrated $\alpha$-sulfofatty acid alkyl ester alkali metal salt pastes, particularly those having WAS contents of 60 to 70% by weight, the hydrogen peroxide and the bleach activator optionally used are introduced together with the sulfonation product and the aqueous alkali metal hydroxide solution into an aqueous phase containing 0 to 70% by weight washing active substance at a pH value in the range from 2 to 8 and WAS contents of 60 to 70% by weight and preferably 60 to 65% by weight are established during the neutralization of the acidic α-sulfofatty acid ester.

In one particular embodiment of the invention, hydrogen peroxide, sulfonation product, aqueous alkali metal hydroxide solution and optionally bleach activator are simultaneously introduced into an aqueous phase which initially contains 0% by weight washing-active substance, i.e. consists of water.

If solutions having a washing-active substance content which is different from 0 and may be as high as 55% by weight are used as aqueous phase at the beginning of neutralization, these solutions are adjusted beforehand to a pH value in the range from 2 to 8.

In one preferred embodiment of the invention, a pH value in the range from 2 to 6 and preferably in the range from 3 to 5 is maintained in the aqueous phase during neutralization until a content of washing-active substance of 55 to 65% by weight and preferably 60 to 65% by weight is reached. In addition, a pH value in the range from 5 to 8 and preferably in the range from 5.5 to 7.5 is preferably adjusted and maintained in the aqueous phase after a washing-active substance content of 55 to 65% by weight and preferably 60 to 65% by weight has been reached.

In another preferred embodiment of the invention, hydrogen peroxide, sulfonation product, aqueous alkali metal hydroxide solution and optionally bleach activator are simultaneously introduced into an aqueous phase initially containing at least 55% by weight washing-active substance. In this case, a pH value of 5.5 to 7.5 is preferably maintained in the aqueous phase during neutralization.

The neutralization of the α-sulfofatty acid alkyl ester is carried out at temperatures below 95° C. and preferably at temperatures in the range from 60° to 80° C.

Neutralization of the acidic α-sulfofatty acid alkyl ester is best carried out in a neutralization loop of the type diagrammatically illustrated in FIG. 1. The predominant part of the aqueous phase is accommodated in the stirred tank 1 in which it is continuously stirred by the stirrer 2. Aqueous phase is continuously removed by the circulation pump 4 via the circulation pipe 3 and is cooled to the necessary extent in the cooler 5 provided to control the reaction temperature. The α-sulfofatty acid alkyl ester to be neutralized is introduced into the stream of the circulated aqueous phase through the pipe 6. Aqueous alkali metal hydroxide solution having a standard concentration, for example 50% by weight sodium hydroxide solution, is introduced into the circuit through the pipe 7. The concentration of the standard alkali metal hydroxide solution can be reduced to the particular value required before it is introduced into the product circuit by the introduction of water through the pipe 8. Aqueous hydrogen peroxide solution can be introduced into the neutralization circuit through the pipe 9. Bleach activators optionally added may be introduced into the circulating aqueous phase through the pipe 10. The mixture of acidic α-sulfofatty acid alkyl ester, alkali metal hydroxide solution and circulated aqueous phase then enters the mixer 11 for further homogenization and, from the mixer 11, is transported into the stirred tank 1 through the last section of the circulation pipe 3. The α-sulfofatty acid alkyl ester alkali metal salt paste formed during neutralization can be removed through the pipe 12. A neutralization loop of the type described in the foregoing may be made up exclusively of standard units, fittings and pipes. Known measuring and control methods for chemical processes may be used for the necessary monitoring of the pH value and the reaction temperature and for controlling the product and coolant flows.

The after-reaction which follows neutralization may be carried out in a heatable stainless steel vessel of known type provided with a stirrer. After leaving the neutralization loop, the neutralization product is best defoamed in a vessel kept under reduced pressure, for example 300 to 400 mbar, before it is introduced into the after-reactor.

Using the described neutralization loop, the neutralization process may readily be set up for continuous operation. In this case, the aqueous phase pump-circulated in the neutralization loop consists of an α-sulfofatty acid alkyl ester alkali metal salt paste which corresponds to the neutralization product removed from the circuit in its WAS content, its hydrogen peroxide content and its bleach activator content, if any. Acidic α-sulfofatty acid alkyl ester, alkali metal hydroxide solution, hydrogen peroxide solution and, optionally, bleach activator are added to the neutralization circuit at the same rate as neutralization product is removed from the circuit. To maintain a constant WAS content, the standard alkali metal hydroxide solution introduced is diluted to the necessary concentration by addition of water.

In the context of the invention, fatty acid alkyl esters are understood to be lower alkyl esters of saturated fatty acids, more particularly esters of fatty acids containing 10 to 18 carbon atoms and saturated aliphatic alcohols containing 1 to 4 carbon atoms. Basically, individual fatty acid alkyl esters may be used as starting material. In general, however, ester mixtures of the type obtainable from fats and oils of natural origin either by ester cleavage and subsequent esterification with lower alkanols or by transesterification with lower alkanols by known methods are used as the starting material, the corresponding fatty acid methyl ester mixtures being preferred. If the fatty acid ester mixtures obtained in this way have relatively large percentage contents of esters of fatty acids containing less than 10 carbon atoms, these "head-fractionated fatty acid esters" are generally removed by distillation. Apart from the $CH_2$ group in the α-position to the ester group, the fatty acid esters should not contain any sulfatable or sulfonatable groups. For this reason, hydroxyfatty acid esters or mixtures containing hydroxyfatty acid esters are not suitable as starting materials. Fatty acid ester mixtures containing non-negligible quantities of esters of unsaturated fatty acids, more particularly esters having an iodine value above 5, are only suitable as starting materials after saturation of the double bonds in the course of hardening by hydrogenation using known methods. During the hydrogenation, the iodine values of the ester mixtures are preferably reduced to values of 0.2 and lower.

The fatty acid esters are sulfonated with gaseous $SO_3$ as the sulfonating agent at temperatures in the range from 30° to 80° C. The $SO_3$ is contacted with the fatty acid esters after dilution with air or nitrogen, preferably in the form of a gas mixture containing 1 to 10% by volume $SO_3$. The quantity of $SO_3$ is gauged in such a way that the molar ratio of fatty acid ester to $SO_3$ is in the range from 1:1.2 to 1:1.8. This reaction may be carried out in standard reactors suitable for the sulfonation of organic compounds, such as fatty alcohols, alkyl benzenes or olefins, more particularly in falling-film reactors or multistage cascades of stirred tank reactors.

The crude sulfonation product issuing from the sulfonation reactor still does not have the desired degree of sulfonation. For this reason, the crude reaction product is delivered immediately after sulfonation to a suitable apparatus in which it is subjected to a temperature-controlled after-reaction for 20 to 40 minutes and preferably for 25 to 35 minutes with mechanical agitation until the desired degree of sulfonation is reached. The apparatus required for this reaction step may consist of a standard reactor with a heating and cooling circuit, a standard temperature-controlled pipe coil or a standard cascade of stirred tanks. The after-reaction is carried out at temperatures of 60° to 100° C. The sulfonated product may be mechanically agitated during the after-reaction by stirring, by introduction of the product under pressure, by the installation of chicane-like baffles in the apparatus or, where a pipe coil is used, by generation of turbulent flow. The after-reaction of the sulfonated product may be controlled by suitable choice of the parameters mentioned, more particularly the reaction time, in such a way that a degree of sulfonation of at least 90% and preferably from 94 to 98% is reached.

Following the after-reaction, the aged sulfonation product is subjected to neutralization and bleaching in accordance with the invention.

EXAMPLE

The starting material used was a technical palmitic/-stearic acid methyl ester (in % by weight according to chain length in the fatty acid part: 0.2 $C_{12}$; 1.2 $C_{14}$; 61.4 $C_{16}$; 0.9 $C_{17}$; 35.9 $C_{18}$; 0.4 $C_{20}$; average molecular weight 281.5; acid value 1.1; iodine value 0.1; saponification value 202.1). The fatty acid methyl ester was continuously sulfonated with an $SO_3$/air mixture (5% by volume $SO_3$) in a molar ratio of 1:1.25 in a standard falling-film reactor at a temperature of 80° C. The resulting reaction mixture was subjected to an after reaction in a holding-time cascade of four stirred tanks with a holding time of 25 minutes. Thereafter the acid value of the sulfonation product was 198. The degree of sulfonation was 96%.

616 kg water were introduced into and pump-circulated in a neutralization loop of the described type. 6836 kg of the aged sulfonation product described above and 1890 kg 50% by weight sodium hydroxide solution were initially fed into the circuit of the aqueous phase at such a rate that a pH value of 5 was maintained in the aqueous phase. When the WAS content of the aqueous phase had reached 55% by weight, the inflow rates of the sulfonation product and the sodium hydroxide solution were adjusted in such a way that the pH value in the aqueous phase was 6. During introduction of the sulfonation product and the aqueous sodium hydroxide solution, 658 kg 20% by weight aqueous hydrogen peroxide solution (2% by weight, based on expected washing-active substance) were introduced into the neutralization circuit. After the entire acidic sulfonation product had been introduced into the neutralization circuit, the pH value of the aqueous phase was increased to 6.1 by addition of the remaining sodium hydroxide solution. Throughout the neutralization process, the reaction temperature was kept at 90° to 93° C. The aqueous phase could readily be stirred and pump-circulated at any time during the neutralization process.

The neutralized product was pumped off into a closed vessel and defoamed under reduced pressure (approx. 380 mbar) before it was transferred to a stirrer-equipped stainless steel vessel and exposed therein to a temperature of 75° C. for 38 hours while mixing. The degree of lightening as a function of time was monitored by measurement of the Klett color values of samples. The Klett color values were measured on aqueous solutions containing 5% by weight washing-active substance in a 4 cm cuvette using a blue filter (420 nm). The bleaching trend as a function of time is shown in Table 1.

TABLE 1

| Lightening during the bleaching reaction at 75° C. | |
|---|---|
| Reaction time (n) | Klett color value |
| 0 | 640 |
| 12 | 232 |
| 16 | 150 |
| 20 | 130 |
| 38 | 80 |

10,000 kg of a stirrable and pumpable α-sulfofatty acid methyl ester sodium salt paste having a washing-active substance content of 66.0% by weight (54% by weight α-sulfofatty acid methyl ester sodium salt and 12% by weight α-sulfofatty acid disodium salt) were obtained.

What is claimed is:

1. A process for the production of a light colored paste of an α-Sulfofatty acid alkyl ester alkali metal salt which comprises: (1) contacting a fatty acid alkyl ester with gaseous sulfur trioxide to form a partially sulfonated product; (2) maintaining said partially sulfonated product at a temperature of from about 60° C. to about 100° C. for a time to form a sulfonated product having a degree of sulfonation of at least 90%; (3) bleaching and neutralizing said sulfonated product with an aqueous solution comprised of an alkali metal hydroxide and hydrogen peroxide; and (4) treating the mixture from step (3) at a temperature of from about 60° C. to about 90° C. to form said light colored paste.

2. The process of claim 1 wherein the concentration of hydrogen peroxide in said aqueous solution in step (3) is from about 0.5% to about 3% by weight of said sulfonated product.

3. The process of claim 1 wherein in step (3) the concentration of said hydrogen peroxide in the aqueous solution is from about 1.5% to about 2.5% by weight of said sulfonated product.

4. The process of claim 1 wherein said aqueous solution in step (3) is further comprised of a bleach activator.

5. The process of claim 4 wherein said bleach activator is a compound which forms a percarboxylic acid or a percarboxylic acid anion as a result of reaction with hydrogen peroxide.

6. The process of claim 5 wherein said bleach activator is an organic compound having an N-acyl group.

7. The process of claim 6 wherein said acyl group is an acetyl group.

8. The process of claim 5 wherein the concentration of said bleach activator is from about 0.1% to about 5% by weight of said sulfonated product in step (3).

9. The process of claim 1 wherein step (3) is carried out by adding said sulfonated product, hydrogen peroxide, and alkali metal hydroxide to an aqueous phase comprising from 0 to about 55% by weight washing-active substance and having a pH of from about 2 to about 8 to form in step (4) a light colored α-sulfofatty acid alkyl ester alkali metal salt paste comprised of from about 60% to about 70% by weight of washing-active substance.

10. The process of claim 9 wherein said pH is from about 5 to about 8 after a total of washing-active substance of from about 55% to about 65% by weight is achieved.

11. The process of claim 9 wherein said pH is from about 5.5 to about 7.5 after a total of washing-active substance of from about 60% to about 65% by weight is achieved.

12. The process of claim 1 wherein step (3) is carried out below about 95° C.

13. The process of claim 12 wherein step (3) is carried out at a temperature of from about 60° C. to about 90° C.

14. The process of claim 1 wherein said fatty acid alkyl ester is an ester of a fatty acid having from about 10 to about 18 carbon atoms and a saturated aliphatic alcohol having from 1 to about 4 carbon atoms.

15. The process of claim 1 wherein said fatty acid alkyl ester is a methyl ester.

16. The process of claim 1 wherein said fatty acid alkyl ester is a mixture of fatty acid methyl esters obtained by transesterification of natural fats or oils with methanol.

17. The process of claim 1 wherein sulfur trioxide is part of a mixture comprised of up to 10% by volume sulfur trioxide and the remainder air or up to 10% by volume sulfur trioxide and the remainder nitrogen.

18. The process of claim 1 wherein the molar ratio of sulfur trioxide to fatty acid alkyl ester is from about 1.1/1.0 to about 1.8/1.0.

19. The process of claim 18 wherein the molar ratio of sulfur trioxide to fatty acid alkyl ester is about 1.1/1.0.

20. The process of claim 1 wherein the degree of sulfonation in step (2) is from about 94% to about 98%.

* * * * *